United States Patent
Sumi et al.

(10) Patent No.: US 12,089,810 B2
(45) Date of Patent: Sep. 17, 2024

(54) DISTAL END COVER AND ENDOSCOPE

(71) Applicant: OLYMPUS MEDICAL SYSTEMS CORP., Tokyo (JP)

(72) Inventors: Takahiro Sumi, Hachioji (JP); Fumitoshi Hayakawa, Machida (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 397 days.

(21) Appl. No.: 17/686,755

(22) Filed: Mar. 4, 2022

(65) Prior Publication Data

US 2023/0277038 A1  Sep. 7, 2023

(51) Int. Cl.
  *A61B 1/00* (2006.01)
  *A61M 25/01* (2006.01)
  *A61B 17/00* (2006.01)

(52) U.S. Cl.
  CPC ..... *A61B 1/00089* (2013.01); *A61M 25/0147* (2013.01); *A61B 2017/00336* (2013.01)

(58) Field of Classification Search
  CPC ..... A61B 1/00089; A61B 2017/00336; A61M 25/0147
  See application file for complete search history.

(56) References Cited

U.S. PATENT DOCUMENTS

| | | | | |
|---|---|---|---|---|
| 7,762,949 B2* | 7/2010 | Nakao | ................ | A61B 1/00073 600/125 |
| 11,096,558 B2* | 8/2021 | Yamaya | ................ | G02B 23/26 |
| 11,116,385 B2* | 9/2021 | Hosogoe | ............ | G02B 23/2423 |
| 11,147,433 B2* | 10/2021 | Hayakawa | ......... | G02B 23/2476 |
| 11,439,295 B2* | 9/2022 | Hosogoe | ............ | A61B 1/00089 |
| 2017/0000317 A1* | 1/2017 | Iizuka | .................. | A61B 1/0615 |
| 2017/0000319 A1* | 1/2017 | Iizuka | .................... | A61B 1/018 |
| 2017/0238789 A1* | 8/2017 | Iizuka | .................... | A61B 1/018 |
| 2018/0228348 A1* | 8/2018 | Yamaya | ................ | G02B 23/16 |
| 2018/0289245 A1* | 10/2018 | Yamaya | ............. | G02B 23/2476 |
| 2018/0317741 A1* | 11/2018 | Yamaya | ............. | G02B 23/24 |
| 2018/0317742 A1* | 11/2018 | Yamaya | ............. | A61B 1/00098 |
| 2019/0015172 A1* | 1/2019 | Yamaya | ................ | A61B 90/03 |
| 2019/0142242 A1* | 5/2019 | Yamaya | ............. | A61B 1/00089 600/101 |

(Continued)

FOREIGN PATENT DOCUMENTS

| | | | |
|---|---|---|---|
| JP | 3626550 B2 | 3/2005 | |
| JP | 4855824 B2 | 1/2012 | |

(Continued)

*Primary Examiner* — John P Leubecker
*Assistant Examiner* — Jae Woo
(74) *Attorney, Agent, or Firm* — Oliff PLC

(57) ABSTRACT

A distal end cover includes a cover body having a cylindrical shape. The cover body includes first and second body portions, a first opening formed in the first body portion and the second body portion, a second opening that can receive a distal end portion of an insertion portion of an endoscope and is formed on a side opposite to the first body portion with respect to the second body portion, a finger hook portion forming a portion of the first opening, a first thin wall portion forming a portion of the first opening, and a second thin wall portion. When a load is applied to the finger hook portion to expand the first opening, a force in a tensile direction is applied to the first thin wall portion, and a force in a shearing direction is applied to the second thin wall portion.

17 Claims, 14 Drawing Sheets

(56) References Cited

U.S. PATENT DOCUMENTS

| | | | | |
|---|---|---|---|---|
| 2019/0208992 | A1* | 7/2019 | Yamaya | ............... A61B 1/122 |
| 2019/0216299 | A1* | 7/2019 | Hayakawa | ............ A61B 1/018 |
| 2020/0037860 | A1* | 2/2020 | Yamaya | ............ A61B 1/00098 |

FOREIGN PATENT DOCUMENTS

| | | |
|---|---|---|
| JP | 6099851 B1 | 3/2017 |
| JP | 6368888 B1 | 8/2018 |
| JP | 6438177 B1 | 12/2018 |
| JP | 2020-151521 A | 9/2020 |

* cited by examiner

DISTAL END COVER AND ENDOSCOPE

BACKGROUND

1. Technical Field

The present disclosure relates to a single-use distal end cover that is mounted on a distal end rigid portion provided at a distal end of an endoscope, and relates to an endoscope.

2. Description of the Related Art

A disposable distal end cover is mounted on an endoscope. The disposable distal end cover is used in a state of being mounted on a distal end portion of an insertion portion. Such a distal end cover is partially locked to the endoscope, thus being prevented from being easily removed from the endoscope. Therefore, there is a known distal end cover that can be easily removed from an end portion of the insertion portion by forming a portion having a thin wall thickness.

For example, Japanese Patent Application Laid-Open Publication No. 2020-151521 discloses a technique where a recessed portion having a smaller wall thickness than other portions is formed on a distal end cover in a circumferential direction to provide a flexible portion that can be easily deflected by being pushed by fingers, for example. With such a configuration, a user can easily remove a distal end cap from a distal end portion by deforming the distal end cap.

SUMMARY

One aspect of the present disclosure is directed to a distal end cover including: a cover body having a bottomed cylindrical shape, the cover body including a first body portion and a second body portion forming a cylindrical peripheral surface; a first opening formed in the first body portion and the second body portion; a second opening formed on a side opposite to the first body portion with respect to the second body portion, a distal end portion of an insertion portion of an endoscope being inserted into the second opening; a finger hook portion provided in the second body portion and forming a portion of the first opening; a first thin wall portion provided in the first body portion and forming a portion of the first opening, a force in a tensile direction being applied to the first thin wall portion in expanding the first opening by applying a load to the finger hook portion; and a second thin wall portion provided in the second body portion, a force in a shearing direction being applied to the second thin wall portion in expanding the first opening by applying the load to the finger hook portion.

Another aspect of the present disclosure is directed to an endoscope including: an insertion portion having a longitudinal axis and configured to be inserted into a subject; a distal end portion provided at a distal end of the insertion portion; and a distal end cover detachably mounted on the distal end portion, wherein the distal end cover includes a cover body having a bottomed cylindrical shape, the cover body including a first body portion and a second body portion forming a cylindrical peripheral surface, a first opening formed to communicate with the first body portion and the second body portion, a second opening formed on a side opposite to the first body portion with respect to the second body portion, the distal end portion being inserted into the second opening, a finger hook portion provided in the second body portion and forming a portion of the first opening, a first thin wall portion provided in the first body portion and forming a portion of the first opening, a force in a tensile direction being applied to the first thin wall portion in expanding the first opening by applying a load to the finger hook portion, and a second thin wall portion provided in the second body portion, a force in a shearing direction being applied to the second thin wall portion in expanding the first opening by applying the load to the finger hook portion.

DETAILED DESCRIPTION OF THE PREFERRED EMBODIMENT

In general, when an unexpected force is applied to a distal end cover in mounting the distal end cover, for example, there is a possibility of a thin wall portion being easily broken. Therefore, there is a possibility of the distal end cover being brought into an unusable state against intention of a user.

A distal end cover and an endoscope of the present disclosure described below can achieve a distal end cover of an endoscope and an endoscope that can be prevented from being brought into an unusable state against intention of a user.

Hereinafter, description will be made with reference to drawings for an embodiment of the endoscope, being an insertion device according to one aspect of the present disclosure and for an embodiment of the distal end cover mounted on a distal end of an insertion portion of the endoscope. Note that a configuration of the present disclosure is not limited by the following embodiment.

In the present embodiment, a side-viewing duodenoscope is shown as an example of the endoscope. The endoscope is applicable to various so-called flexible endoscopes in addition to a digestive organ endoscope, and is also applicable to a so-called rigid endoscope. The digestive organ endoscope is inserted into upper or lower digestive organs of a living body and hence, an insertion portion has flexibility. The so-called rigid endoscope is used in surgical applications, and includes a rigid insertion portion.

The present disclosure is also applicable to various endoscopes, such as an industrial endoscope, in addition to a medical endoscope. In other words, the present disclosure is a technique that is applicable to an endoscope where movable members, such as an image pickup unit and a treatment instrument raising base (forceps elevator), are mounted on a distal end portion of an insertion portion.

In the description made hereinafter, drawings are schematic views. Note that a relationship of dimensions of the respective elements and a ratio between the respective elements, for example, may differ from actual ones. The relationship of dimensions and the ratio may be partially different between drawings.

EMBODIMENT

Figure 1:
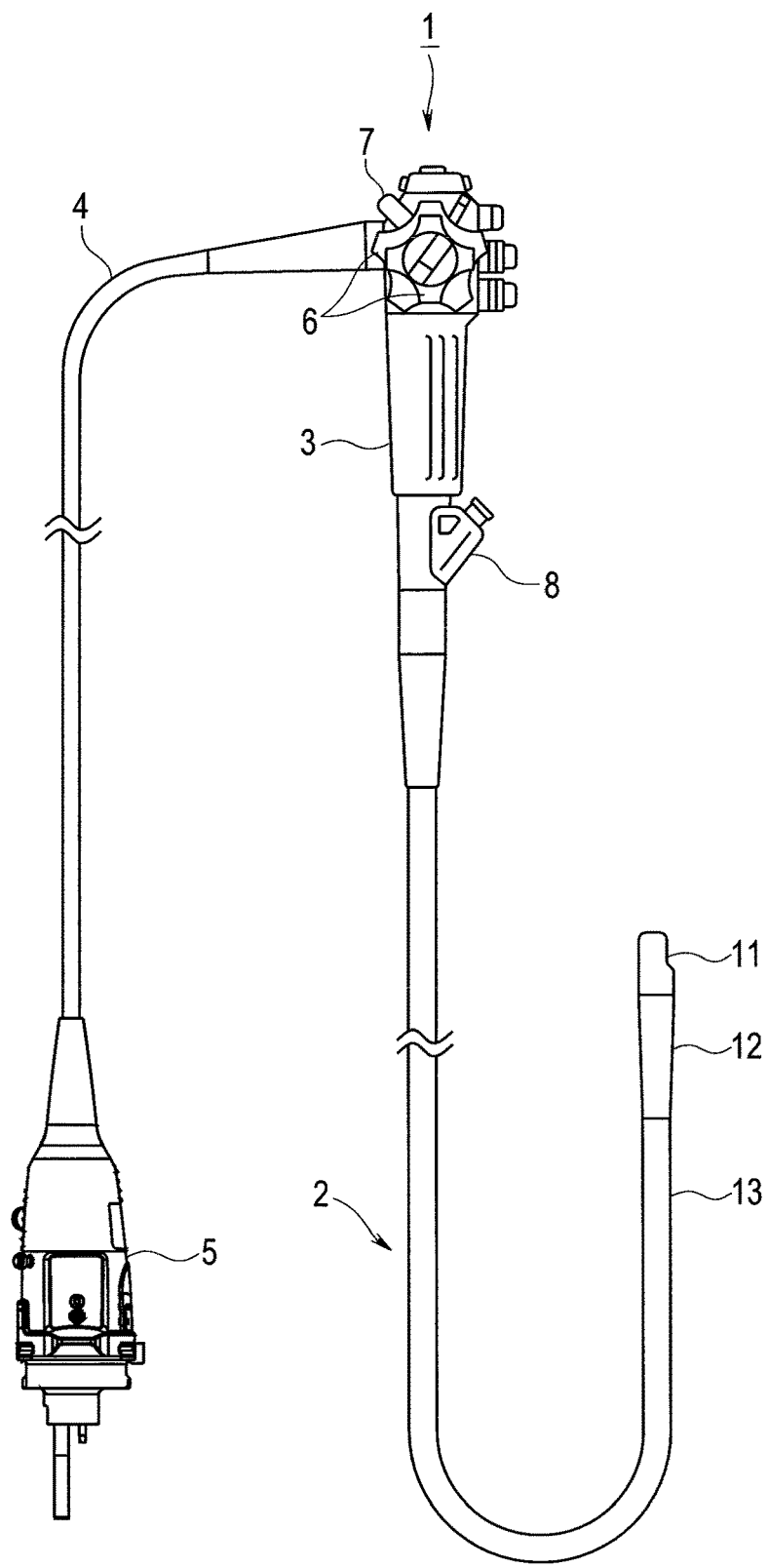
FIG. 1 is a schematic view showing a configuration of an endoscope according to one embodiment.

As shown in FIG. 1, an endoscope 1 being an insertion device of the present embodiment includes an insertion portion 2, an operation portion 3, a universal cord 4, and an endoscope connector 5.

The insertion portion 2 includes an image pickup unit, an illumination unit, and the like at a distal end, and is inserted into a subject. The operation portion 3 is continuously connected with a proximal end side of the insertion portion 2. The universal cord 4 extends from a side portion of the operation portion 3. The endoscope connector 5 is continuously connected with the universal cord 4. The endoscope connector 5 is connected to an observation device, a light source device, and the like. The observation device controls the endoscope 1. The light source device supplies illumination light to the endoscope 1.

The insertion portion 2 includes a distal end portion 11, a bending portion 12, and a flexible tube portion 13 in this order from a distal end side. The bending portion 12 is configured to be bendable according to an operation of a bending knob 6 provided in the operation portion 3. The flexible tube portion 13 has flexibility.

The flexible tube portion 13 is continuously connected with a distal end side of the operation portion 3. The endoscope 1 may be an ultrasound endoscope that includes an ultrasound transducer in the distal end portion.

Figure 3:
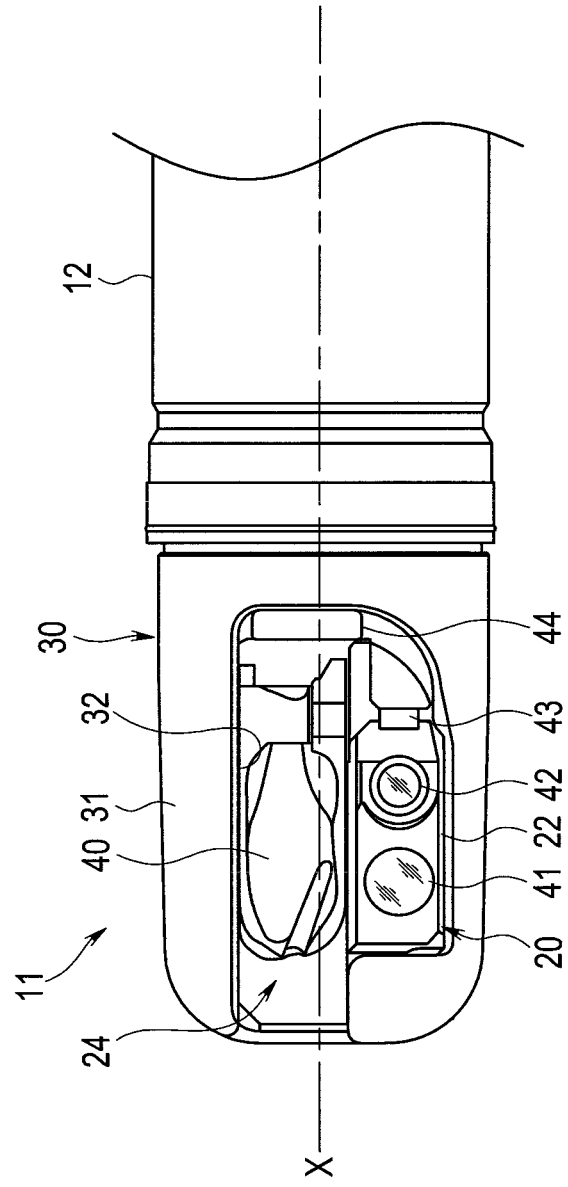
FIG. 3 is a top plan view showing the configuration of the distal end portion on which the distal end cover is mounted.

The distal end portion 11 has an opening, and is provided with a treatment instrument raising base (also referred to as a "forceps raising base") 40 that can vary a direction in which a forceps needle or the like, being a treatment instrument, extends from the opening (see FIG. 3). The distal end portion 11 also has a treatment instrument channel opening and the like that communicate with the opening.

The distal end portion 11 includes, in a side portion of the opening, an illumination lens 41 being an illumination window, an observation lens 42 being an observation window, and a gas/liquid feeding nozzle 43. In other words, the endoscope 1 is a side-viewing endoscope where a visual field direction is a lateral direction. The endoscope 1 may be an oblique viewing endoscope where a visual field direction is a forward oblique direction.

The operation portion 3 has a forceps insertion port 8 through which a forceps needle or the like, being a treatment instrument, is inserted into a subject. The operation portion 3 includes an operation lever 7 that operates the treatment instrument raising base 40 provided in the distal end portion 11.

A forceps insertion passage is provided in the insertion portion 2, and the forceps insertion port 8 forms an insertion port of a treatment instrument channel. In other words, the endoscope 1 is an endoscope through which a treatment instrument can be inserted.

Figure 2:
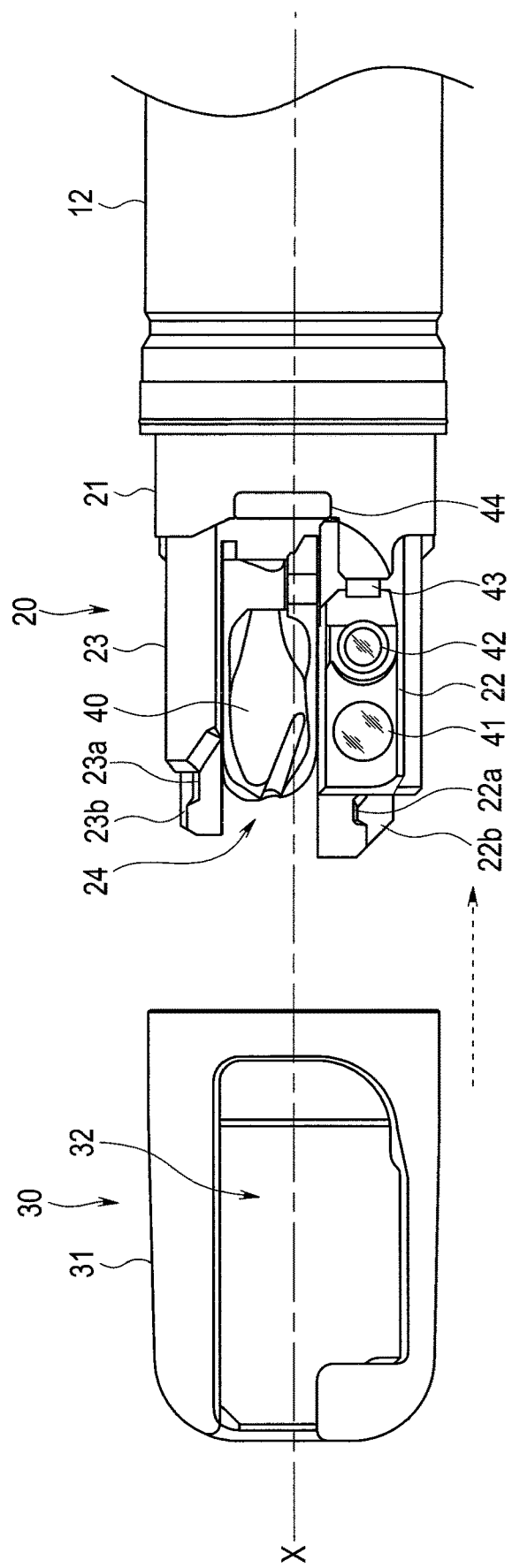
FIG. 2 is a top plan view showing configurations of a distal end cover and a distal end portion.

As shown in FIG. 2 and FIG. 3, the distal end portion 11 is configured such that a distal end cover 30 of the endoscope 1 is mounted on a distal end rigid member 20.

The distal end cover 30 is a sheath-shaped member that covers a predetermined area of an outer surface of the distal end rigid member 20, and has predetermined elasticity to allow the distal end cover 30 to be detachably mounted on the distal end rigid member 20. The distal end cover 30 is made of resin, for example, having electrical insulation properties.

The distal end cover 30 is made of translucent or transparent resin. Such a configuration allows a user of the endoscope 1 to easily visually recognize whether the distal end cover 30 is correctly mounted on the distal end rigid member 20 at a predetermined position. However, the distal end cover 30 is not limited to a cover made of translucent or transparent resin. The distal end cover 30 may be formed with a contrast agent having X ray transmittance significantly different from X ray transmittance of the tissue of a subject, such as a human body, being mixed into resin used for forming the distal end cover 30. The contrast agent may be mixed into the entire distal end cover 30 or may be mixed into a part of the distal end cover 30.

The distal end rigid member 20 is a rigid member that forms the distal end portion 11. The distal end rigid member 20 includes a distal end portion body 21 and a first arm portion 22 and a second arm portion 23, being a pair of arm portions. The distal end portion body 21 is disposed on a proximal end side of the distal end rigid member 20. The first arm portion 22 and the second arm portion 23 are provided on a distal end side of the distal end portion body 21.

The first arm portion 22 and the second arm portion 23 protrude from the distal end portion body 21 toward the distal end side along a longitudinal axis X of the insertion portion 2, and forms a raising base accommodation space 24 being a space formed between the first arm portion 22 and the second arm portion 23. The treatment instrument raising base 40 is turnably disposed in the raising base accommodation space 24.

The distal end portion body 21 has a columnar outer shape. A proximal end of the distal end portion body 21 is connected to a distal end of the bending portion 12. A locking pawl 44 (locking portion) protruding upward is provided on the distal end portion body 21 in a region on an upper surface of an outer peripheral surface. The locking pawl 44 is a portion that locks a proximal end of an opening 32 of the distal end cover 30.

The raising base accommodation space 24 is disposed so as to be open in three directions, that is, in a distal end direction and upward and downward directions. In other words, the first arm portion 22 and the second arm portion 23 are arranged to extend in a direction along an X axis, being a longitudinal axis, with the raising base accommodation space 24 interposed between the first arm portion 22 and the second arm portion 23.

In the present embodiment, the first arm portion 22 is disposed on a right side of the raising base accommodation space 24 as viewed in a front direction, being a direction from a distal end of the insertion portion 2. The second arm portion 23 is disposed on a left side of the raising base accommodation space 24. Left and right positions, where the first arm portion 22 and the second arm portion 23 are disposed, may be reversed.

The first arm portion 22 and the second arm portion 23 are provided in a cantilever manner, and no member extends between the first arm portion 22 and the second arm portion 23. A columnar or wall-shaped member may be provided between the first arm portion 22 and the second arm portion 23 to connect both portions with each other.

The illumination lens 41, the observation lens 42, and the gas/liquid feeding nozzle 43 are provided on an upper surface of the first arm portion 22. The observation lens 42 is provided to pick up images of an object. The illumination lens 41 is provided to emit illumination light toward the object.

Photographing light from the object which is incident from the observation lens 42 is photographed by the image pickup unit (not shown in the drawing), such as a camera module, provided in the distal end portion 11.

Observation means is not limited to the image pickup unit, and may be an image fiber provided in the insertion portion 2. A visual field of the observation lens 42 is a lateral direction of the insertion portion 2, so that the endoscope 1 is a side-viewing endoscope.

The illumination lens 41 projects, toward the subject, illumination light transmitted through a light guide (not shown in the drawing) inserted through and disposed in the insertion portion 2. Illumination means is not limited to the light guide, and may be an LED module incorporated in the distal end portion 11.

The gas/liquid feeding nozzle 43 is a portion that ejects fluid, such as gas or liquid, toward the illumination lens 41 and the observation lens 42.

The treatment instrument raising base 40 is turnably provided in the raising base accommodation space 24. The treatment instrument raising base 40 is a so-called tongue-shaped member that extends in one direction from a rotary shaft. With a predetermined operation of the operation lever 7 of the operation portion 3, the treatment instrument raising base 40 turns to a raised state and to an inverted state. A pulling and loosening member (not shown in the drawing), such as a wire, is disposed in the operation portion 3 and the insertion portion 2 to transmit the operation performed by the operation lever 7 to the treatment instrument raising base 40. A distal end side of the pulling and loosening member is accommodated in the distal end portion 11. However, the distal end side of the pulling and loosening member may be disposed outside the distal end portion 11.

Description will be made for a structure of holding the distal end cover 30 so as not to fall off in a state where the distal end cover 30 is mounted on the distal end rigid member 20.

Figure 4:
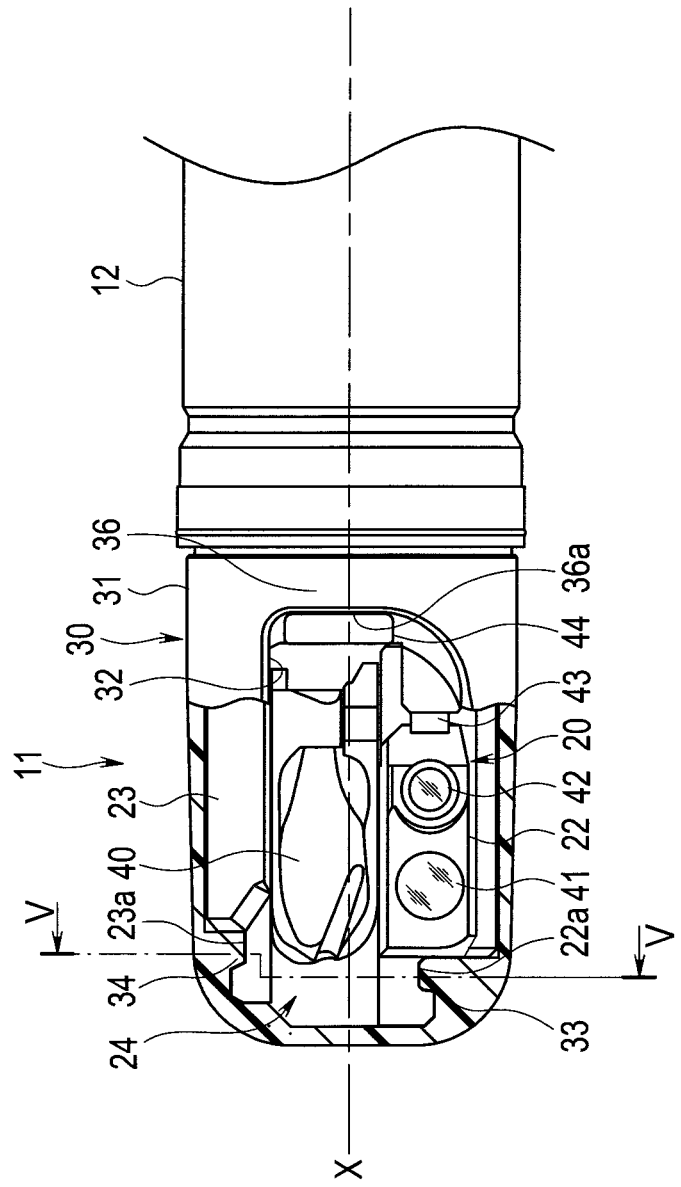
FIG. 4 is a partial cross-sectional view showing the configuration of the distal end portion on which the distal end cover is mounted.

As shown in FIG. 4, the first arm portion 22 has an engagement groove 22a having a recessed shape. The engagement groove 22a has a recessed shape recessed from an outer side toward an inner side. The engagement groove 22a is formed in the up-and-down direction orthogonal to (intersecting with) the longitudinal axis X, and is disposed at a distal end portion of the first arm portion 22.

The second arm portion 23 also has an engagement groove 23a having a recessed shape. The engagement groove 23a also has a recessed shape recessed from an outer side toward an inner side. The engagement groove 23a is formed in the up-and-down direction orthogonal to the longitudinal axis X, and is disposed at a distal end portion of the second arm portion 23.

The engagement groove 22a and the engagement groove 23a are formed to recess inward in a lateral direction, thus forming opposing recessed portions. In other words, the engagement groove 22a and the engagement groove 23a are portions formed on the outer surface of the distal end rigid member 20 and having a recessed shape. The engagement groove 22a and the engagement groove 23a are open outward in respective opposite directions along a direction substantially orthogonal to (intersecting with) the longitudinal axis X of the insertion portion 2.

These engagement grooves 22a, 23a are respectively portions to be engaged with locking pawls 33, 34, being protruding-shaped locking portions of the distal end cover 30. The locking pawls 33, 34 will be described later.

Figure 5:
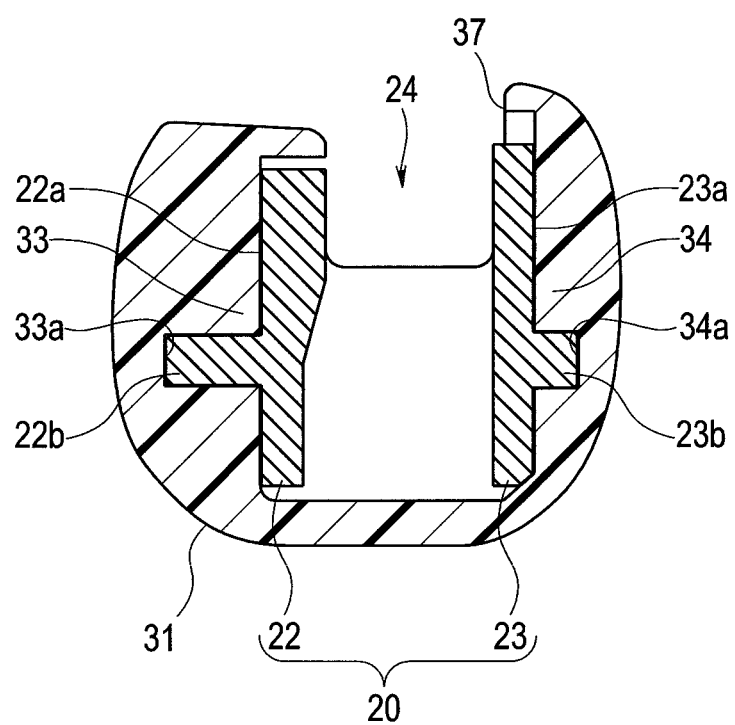
FIG. 5 is a cross-sectional view showing the configuration of the distal end portion taken along a line V-V in FIG. 4.

As shown in FIG. 5, the first arm portion 22 and the second arm portion 23 are respectively provided with a first rib 22b and a second rib 23b having a protruding shape and preventing rotation of the distal end cover 30. More specifically, the first arm portion 22 of the distal end rigid member 20 is provided with the first rib 22b protruding in an outward direction. The second arm portion 23 of the distal end rigid member 20 is also provided with the second rib 23b protruding in an outward direction.

These first rib 22b and the second rib 23b are configured to prevent the distal end cover 30 from rotating relative to the distal end rigid member 20 in the state where the distal end cover 30 is mounted on the distal end rigid member 20.

Although detailed description will be made later, the distal end cover 30 includes rotation stopping portions 33a, 34a on an inner peripheral surface. The rotation stopping portions 33a, 34a are rotation restricting portions that have a recessed shape and respectively engage with the first rib 22b and the second rib 23b. In other words, when a force of rotating the distal end cover 30 relative to the distal end rigid member 20 is generated, rotation of the distal end cover 30 is prevented by engagement of the first rib 22b and the second rib 23b with the rotation stopping portions 33a, 34a.

A detailed configuration of the distal end cover 30 mounted on the distal end rigid member 20 will be described hereinafter with reference to FIG. 4 to FIG. 13.

The distal end cover 30 is a sheath-shaped member where a distal end direction side of a cover body 31 is closed and a proximal end direction side of the cover body 31 is open. In other words, the distal end cover 30 is a cylindrical member having a bottom portion. When the distal end cover 30 is mounted on the distal end rigid member 20, the distal end cover 30 covers a predetermined portion of an outer peripheral surface of the distal end rigid member 20.

Figure 6:
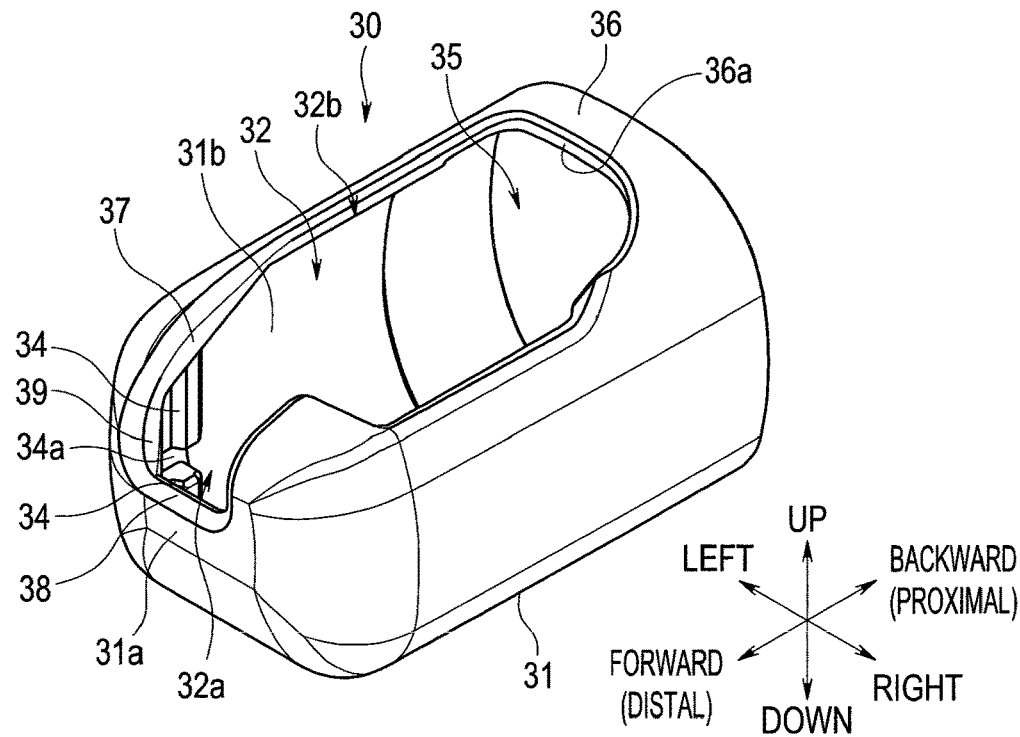
FIG. 6 is a perspective view showing a configuration of the distal end cover as viewed from a distal end side.
Figure 7:
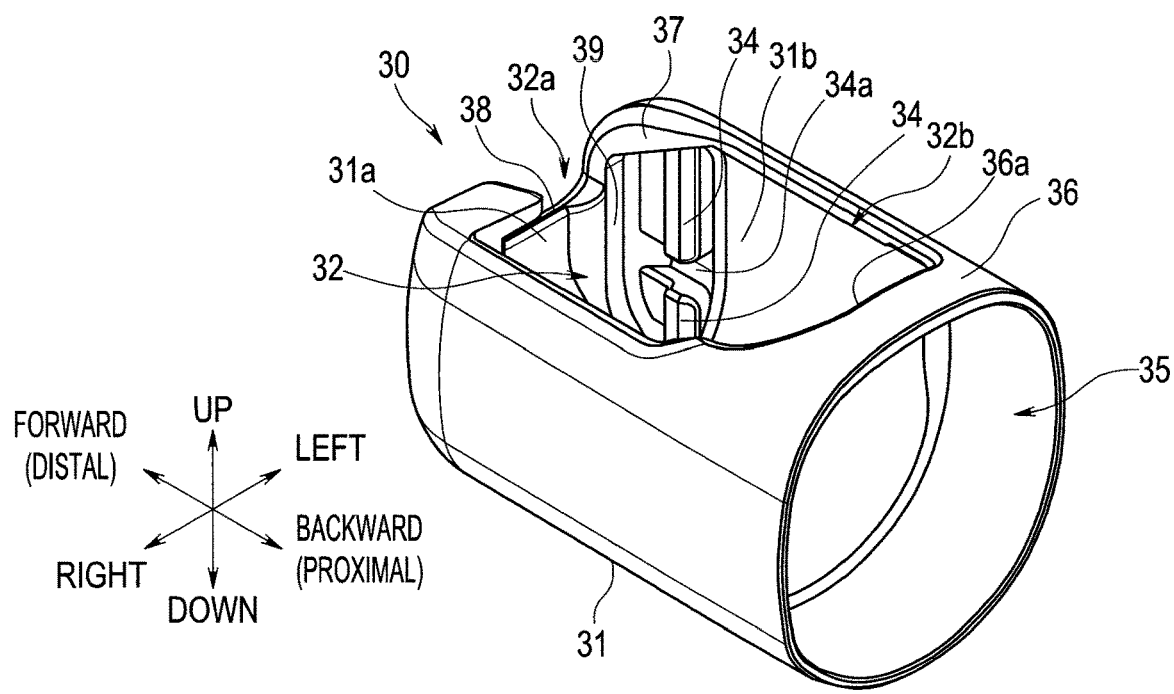
FIG. 7 is a perspective view showing the configuration of the distal end cover as viewed from a proximal end side.
Figure 8:
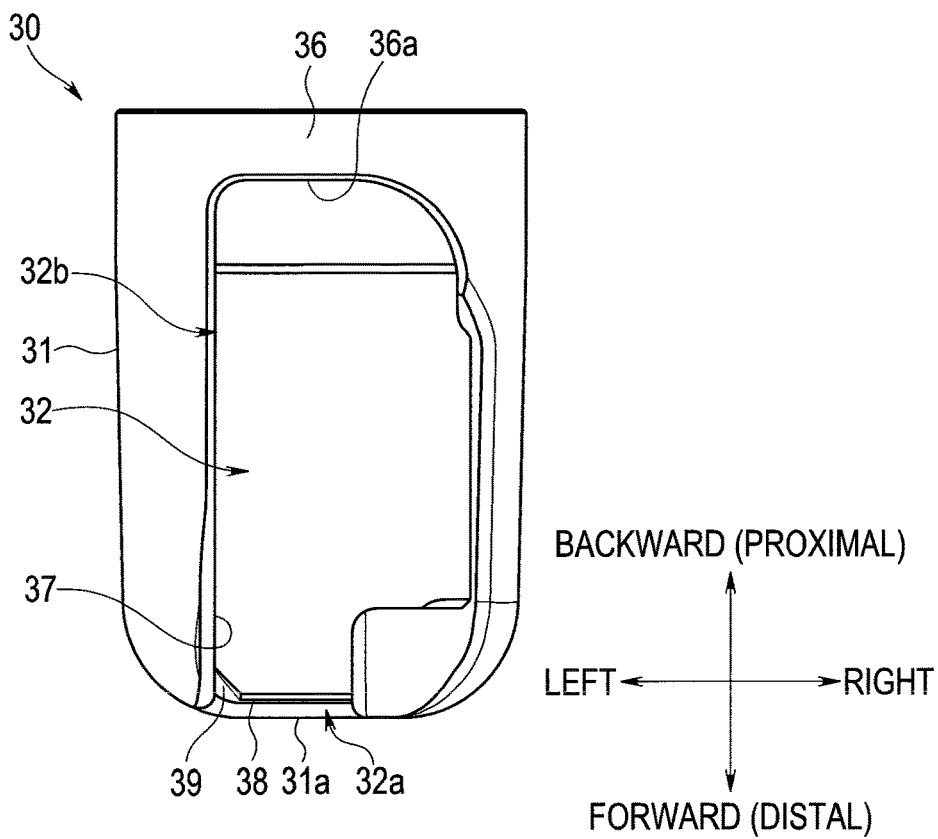
FIG. 8 is a top plan view showing the configuration of the distal end cover.
Figure 9:
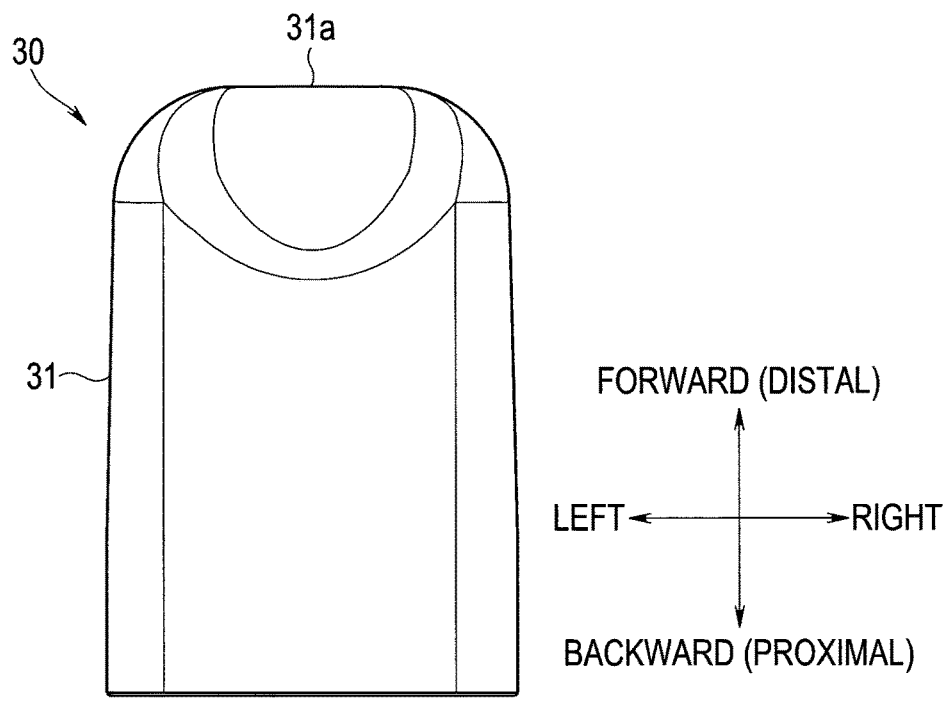
FIG. 9 is a bottom view showing the configuration of the distal end cover.
Figure 10:
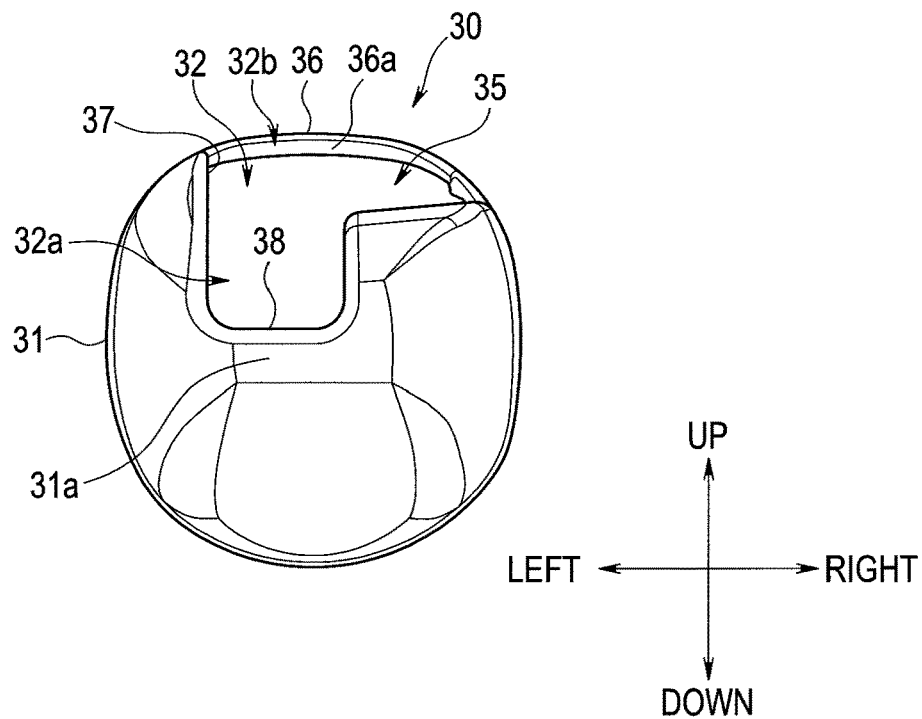
FIG. 10 is a front view showing the configuration of the distal end cover.
Figure 11:
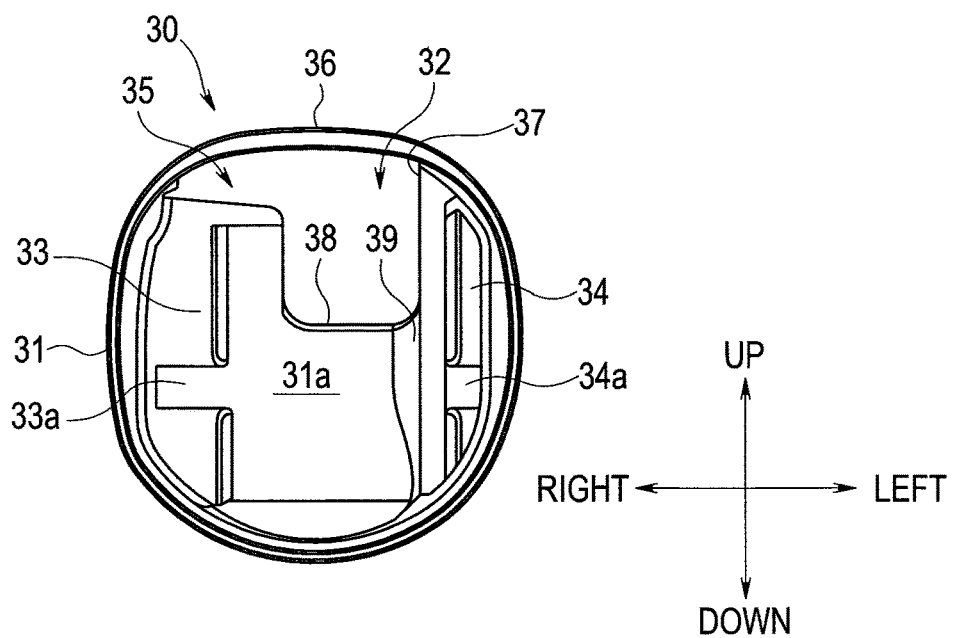
FIG. 11 is a back view showing the configuration of the distal end cover.
Figure 12:
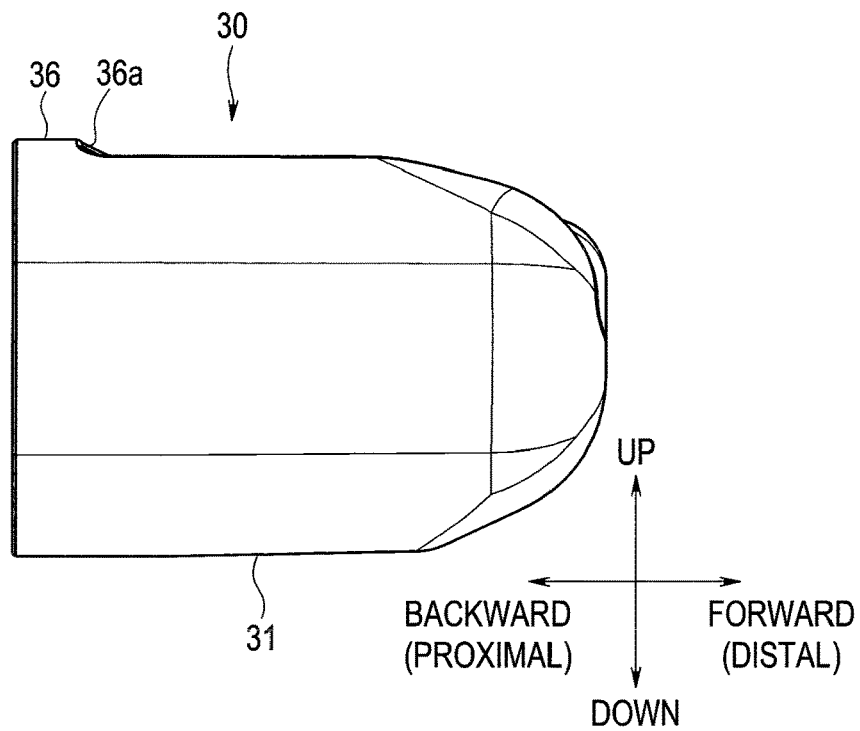
FIG. 12 is a left side view showing the configuration of the distal end cover.
Figure 13:
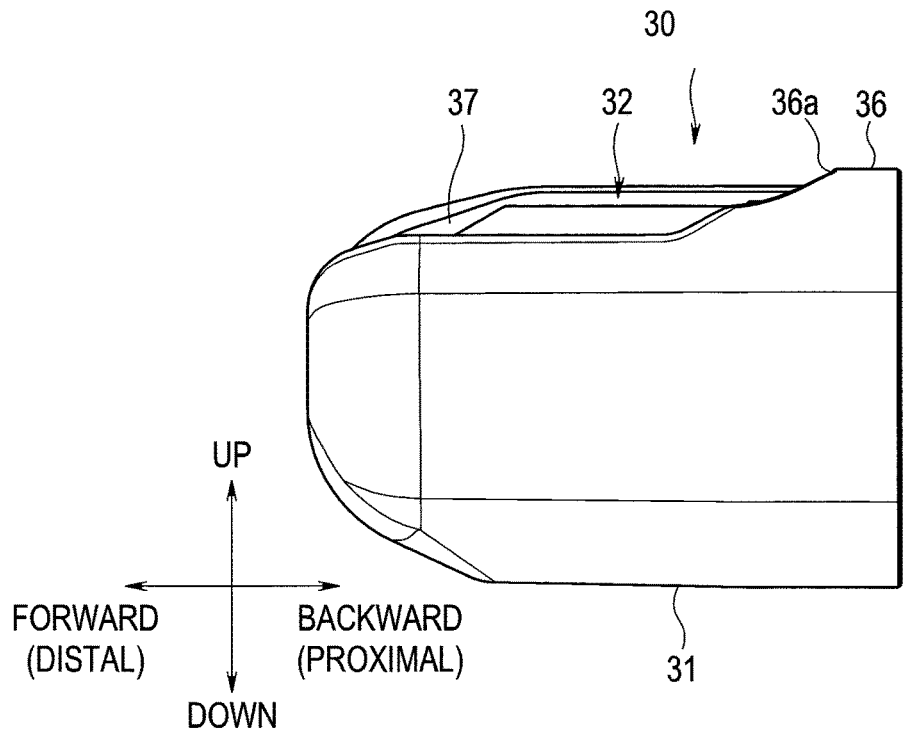
FIG. 13 is a right side view showing the configuration of the distal end cover.

The distal end cover 30 has an insertion port 35 at a proximal end of the cover body 31 (see FIG. 6, FIG. 7, and FIG. 11). When the distal end cover 30 is mounted on the distal end rigid member 20, the distal end rigid member 20 is inserted into the distal end cover 30 via the insertion port 35.

The distal end cover 30 has the opening 32 (first opening) through which the raising base accommodation space 24 is exposed in the state where the distal end cover 30 is mounted on the distal end rigid member 20. In the state where the distal end cover 30 is mounted on the distal end rigid member 20, the illumination lens 41, the observation lens 42, and the gas/liquid feeding nozzle 43 are also exposed through the opening 32.

The opening 32 is a hole portion formed in two surfaces of the cover body 31, in the present embodiment, in a front surface and an upper surface of the cover body 31. In other words, the opening 32 is a hole portion where a distal end opening 32a and an upper surface opening 32b are communicated with each other. A width of the distal end opening 32a in the lateral direction is set to be equal to or larger than a width of the raising base accommodation space 24 in the lateral direction.

In the cover body 31, the opening 32 and the insertion port 35 (second opening) do not communicate with each other, and an annular portion 36 is formed at a proximal end portion of the cover body 31. The annular portion 36 is annularly connected about the longitudinal axis X of the insertion portion 2.

In the state where the distal end cover 30 is mounted on the distal end rigid member 20, a portion of the annular portion 36 disposed on a proximal end side of the locking pawl 44 provided on the distal end portion body 21 is brought into close contact with the outer peripheral surface of the distal end portion body 21. In such a state, the locking pawl 44 protrudes in the opening 32. In other words, in the state where the distal end cover 30 is mounted on the distal end rigid member 20, when the distal end cover 30 moves in the distal end direction relative to the distal end rigid member 20, the locking pawl 44 is brought into contact with an end surface 36a of the annular portion 36 on a distal end side. In other words, the locking pawl 44 prevents the distal end cover 30 from moving in the distal end direction relative to the distal end rigid member 20.

The cover body 31 includes the locking pawls 33, 34 having a protruding shape, the rotation stopping portions 33a, 34a being rotation preventing portions having a recessed shape, and a finger hook portion 37.

The locking pawls 33, 34 are portions having a protruding shape and protruding inward in the lateral direction intersecting with (substantially orthogonal to) the longitudinal axis X from an inner peripheral surface of the cover body 31 (see FIG. 4, FIG. 6, FIG. 7, and FIG. 11).

The locking pawl 33 protrudes from either one of a left inner surface or a right inner surface of the inner peripheral surface of the cover body 31. In the present embodiment, the locking pawl 33 protrudes inward, that is, in a leftward direction, from the right inner surface as viewed in the front direction. In the state where the distal end cover 30 is mounted on the distal end rigid member 20, the locking pawl 33 is disposed in and engages with the engagement groove 22a formed on a right side surface of the first arm portion 22 of the distal end rigid member 20.

In contrast, the locking pawl 34 protrudes from either one of the left inner surface or the right inner surface of the inner peripheral surface of the cover body 31. In the present embodiment, the locking pawl 34 protrudes inward, that is, in a rightward direction, from the left inner surface as viewed in the front direction. In the state where the distal end cover 30 is mounted on the distal end rigid member 20, the locking pawl 34 is disposed in and engages with the engagement groove 23a formed on a left side surface of the second arm portion 23 of the distal end rigid member 20.

As described above, the engagement groove 22a of the first arm portion 22 and the engagement groove 23a of the second arm portion 23 are a pair of recessed portions that are formed on the outer surface of the distal end rigid member 20 at positions near a distal end, and that are open in the respective opposite directions along an axis substantially orthogonal to the longitudinal axis X of the insertion portion 2.

In the state where the distal end cover 30 is mounted on the distal end rigid member 20, the engagement grooves 22a, 23a engage with the pair of locking pawls 33, 34 of the cover body 31, thus preventing the cover body 31 from moving toward the distal end relative to the distal end rigid member 20.

As an example, the case is shown where three locking pawls (the locking pawls 33, 34, 44) hold the distal end cover 30 so as not to fall off from the distal end rigid member 20. However, the number of locking pawls is not limited to three, and one, two, or four or more locking pawls may be used.

The rotation stopping portions 33a, 34a are formed on left and right sides of the cover body 31 such that the rotation stopping portions 33a, 34a respectively divide the locking pawls 33, 34. The rotation stopping portions 33a, 34a are rotation preventing portions formed in a recessed shape.

One rotation stopping portion 33a is provided on a right inner peripheral surface of the cover body 31 as viewed from a front side. The other rotation stopping portion 34a is provided on a left inner peripheral surface of the cover body 31 as viewed from the front side.

These rotation stopping portions 33a, 34a are configured to prevent rotation of the cover body 31 relative to the distal end rigid member 20 about the longitudinal axis X of the insertion portion 2 in the state where the distal end cover 30 is mounted on the distal end rigid member 20.

More specifically, in the state where the distal end cover 30 is mounted on the distal end rigid member 20, the first rib 22b provided on the first arm portion 22 engages with the one rotation stopping portion 33a. In the state where the distal end cover 30 is mounted on the distal end rigid member 20, the second rib 23b provided on the second arm portion 23 engages with the other rotation stopping portion 34a.

By respectively providing the rotation stopping portions 33a, 34a at two places, that is, on the left and right inner peripheral surfaces of the cover body 31 as described above, it is possible to prevent rotation of the cover body 31 relative to the distal end rigid member 20 with certainty when the endoscope 1 is in use.

The finger hook portion 37 of the distal end cover 30 is provided in a periphery portion of the opening 32 in a region extending along the longitudinal axis X of the insertion portion 2. The finger hook portion 37 is a portion provided to input a force of rotating the cover body 31 relative to the distal end rigid member 20 about the longitudinal axis X of the insertion portion 2 in the state where the distal end cover 30 is mounted on the distal end rigid member 20. For example, a force applied by a person's finger F (see FIGS. 14, 15) is inputted.

The finger hook portion 37 is formed in a region above the second arm portion 23 of the distal end rigid member 20 in the state where the distal end cover 30 is mounted on the distal end rigid member 20. In other words, in the present embodiment, the finger hook portion 37 is provided in the periphery portion of the opening 32 in a region on the left side of and above the first arm portion 22 as viewed from the front side.

The finger hook portion 37 is formed to further protrude upward from an upper surface of the second arm portion 23 in a cross-sectional direction orthogonal to (intersecting with) the longitudinal axis X of the insertion portion 2. Further, the finger hook portion 37 is formed to protrude upward from a surface of a portion of the periphery portion of the opening 32 that is disposed above the first arm portion 22, which is disposed on the right side.

Figure 14:
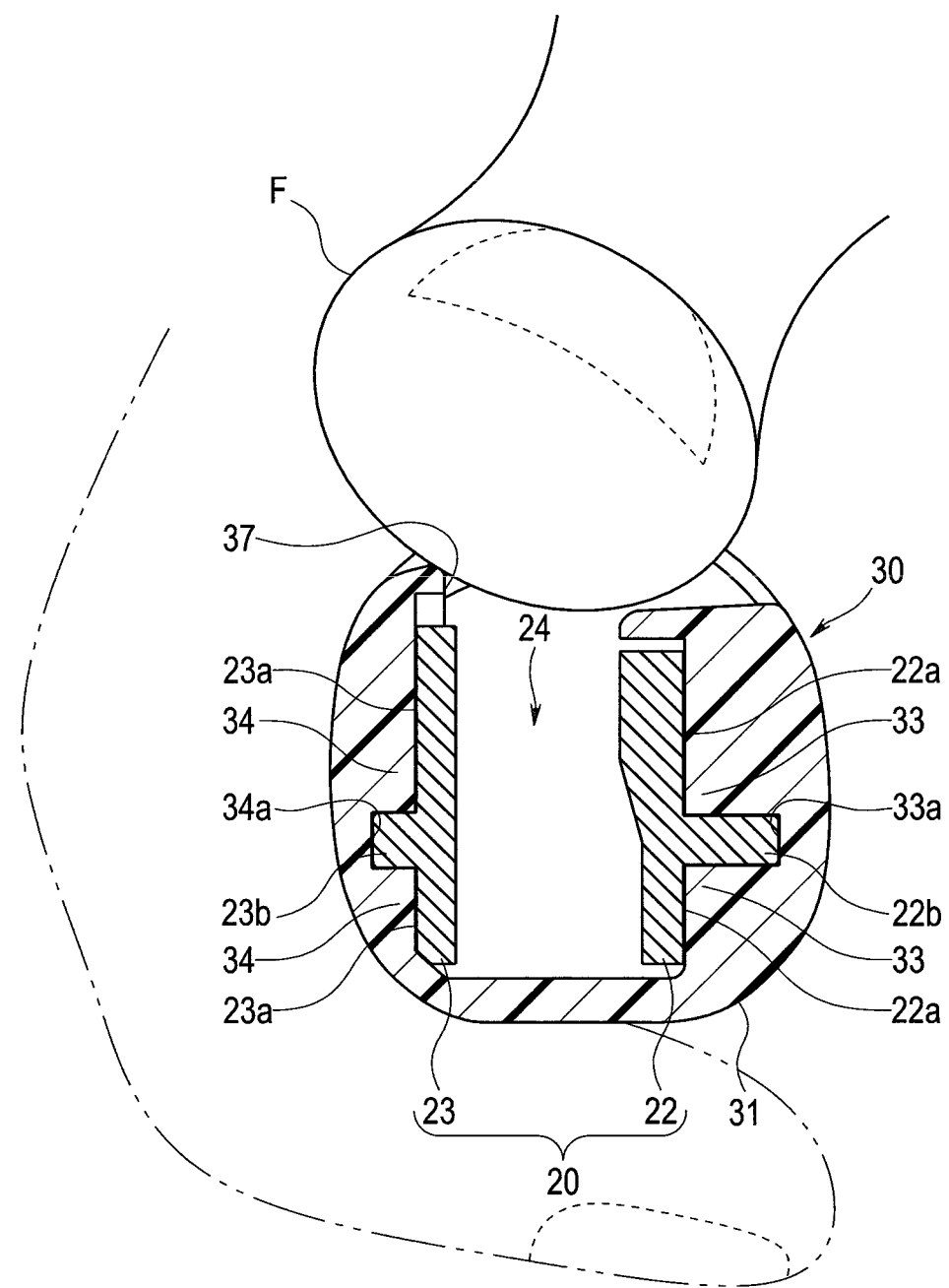
FIG. 14 is a cross-sectional view showing a state of removing the distal end cover from a distal end rigid member.
Figure 15:
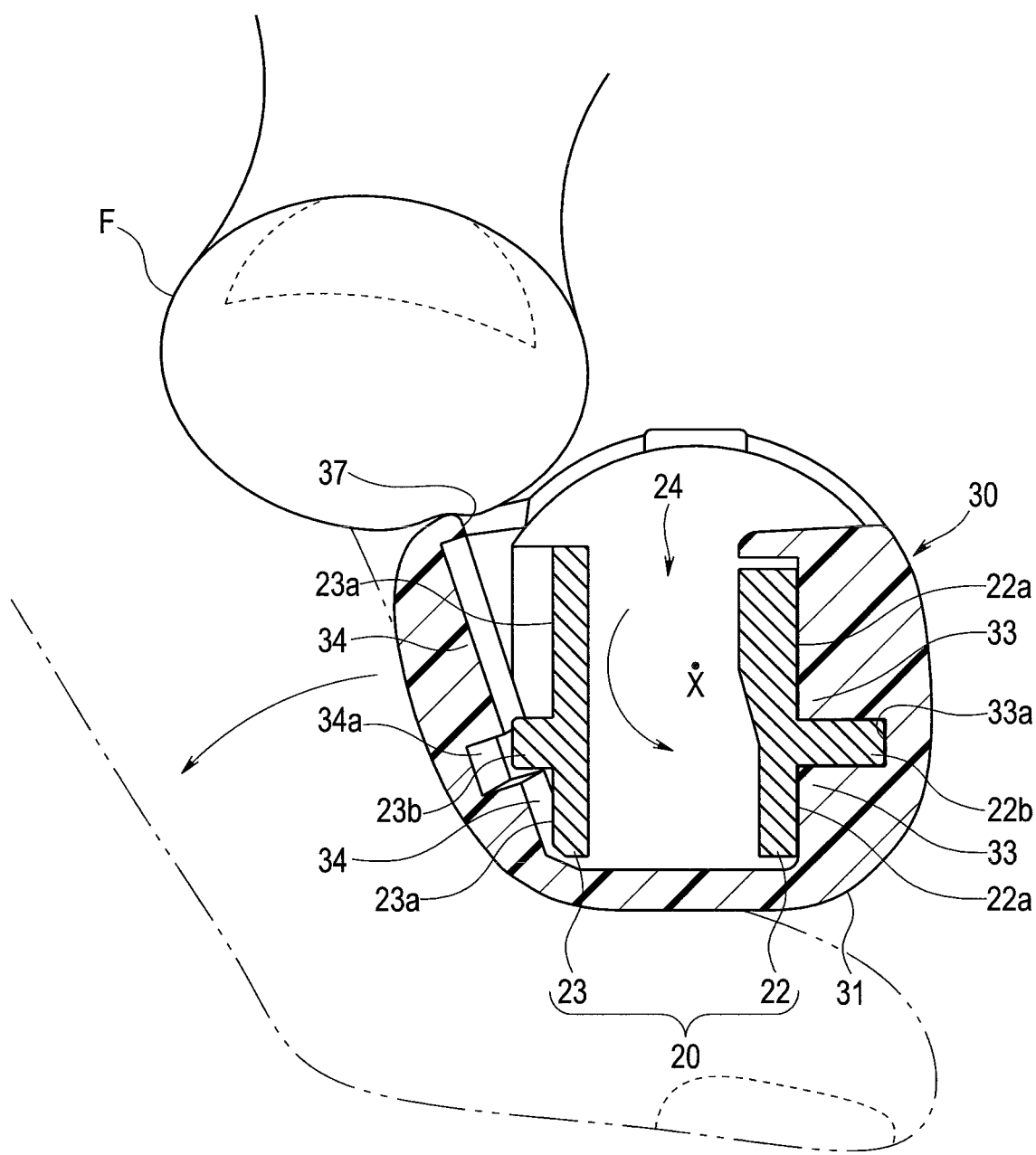
FIG. 15 is a cross-sectional view showing an intermediate state of removing the distal end cover from the distal end rigid member.

The finger hook portion 37 is provided as described above, thus facilitating an inputting operation to the distal end cover 30 by the person's finger F to rotate the distal end cover 30 about the longitudinal axis X of the insertion portion 2 (see FIGS. 14, 15).

A structure of a main part of the distal end cover 30 of the present embodiment will be described hereinafter in detail.

Figure 16:
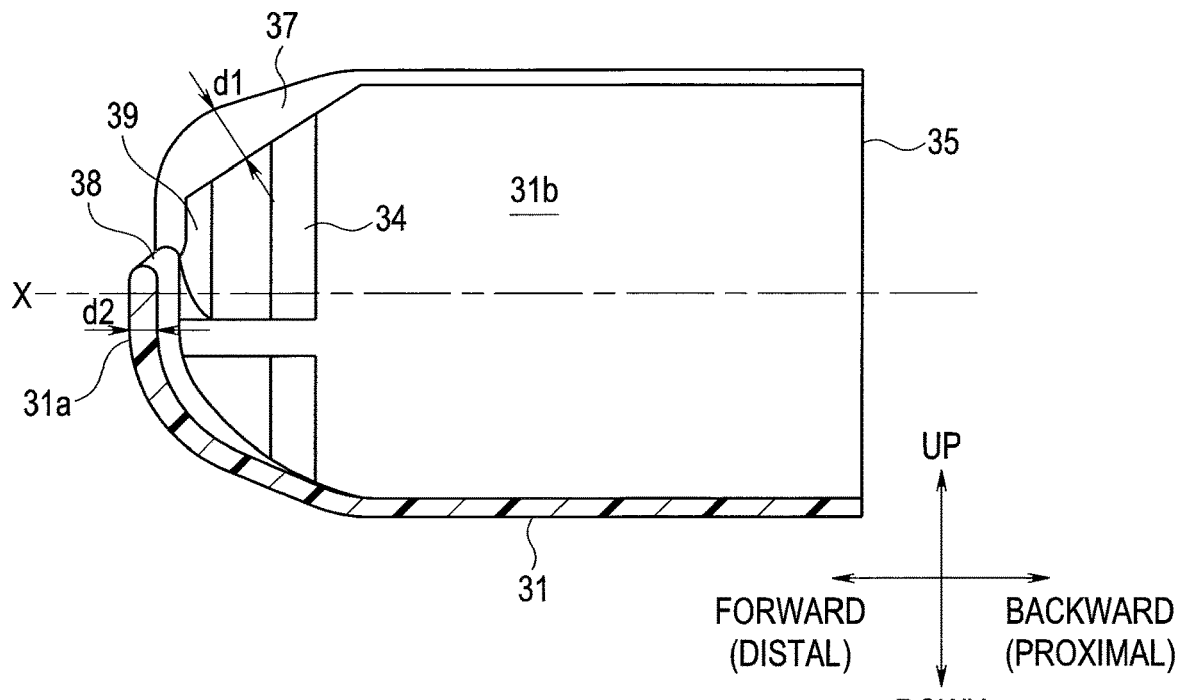
FIG. 16 is a longitudinal cross-sectional view for describing a configuration of a main part of the distal end cover.
Figure 17:
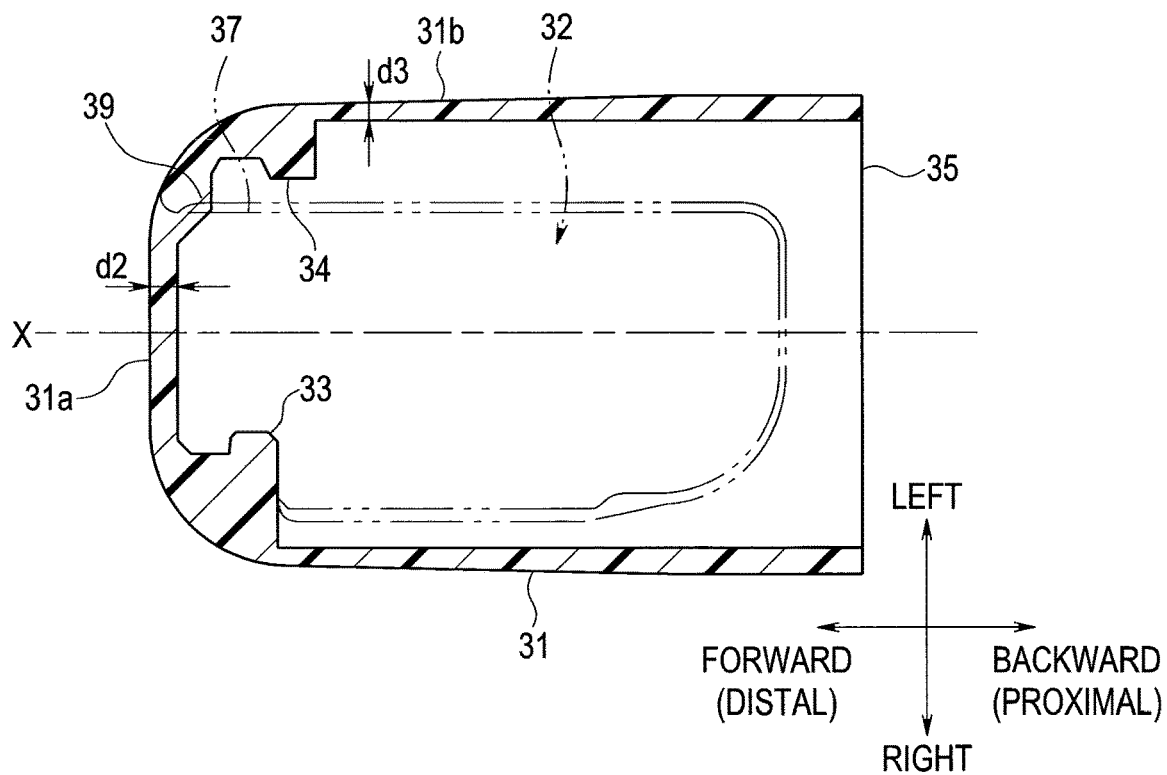
FIG. 17 is a transverse cross-sectional view for describing the configuration of the main part of the distal end cover.

As shown in FIG. 16 and FIG. 17, a thickness d1 of the finger hook portion 37 is set to be larger than a predetermined thickness d2 of a front surface portion 31a forming a portion of the opening 32 of the cover body 31 (d1>d2).

In the present embodiment, the thickness d1 of the finger hook portion 37 is set to be larger than a predetermined thickness d3 of a side surface portion 31b disposed on a left side, being a side where the finger hook portion 37 is disposed (d1>d3). In other words, when the opening 32 is halved on a plane including the longitudinal axis X and being orthogonal to the opening 32, the finger hook portion 37 is provided on the same side as the side surface portion 31b disposed on the left side.

The predetermined thickness d2 of the front surface portion 31a is set to be larger than the predetermined thickness d3 of the side surface portion 31b (d2>d3).

In other words, in the distal end cover 30, the finger hook portion 37 of the cover body 31 is a thick wall portion, and each of the front surface portion 31a (first body portion) and the side surface portion 31b (second body portion) includes a thin wall portion. A wall thickness of the side surface portion 31b (second thin wall portion) disposed on the left side is set to be smaller than a wall thickness of the front surface portion 31a (first thin wall portion). It is preferable that the wall thickness of the second thin wall portion be smaller than the wall thickness of the first thin wall portion. However, the wall thickness of the second thin wall portion may be equal to the wall thickness of the first thin wall portion.

With such a configuration, when the opening 32 is expanded by applying a load to the finger hook portion 37 in the outward direction by the person's finger F (see FIG. 14 and FIG. 15) to remove the distal end cover 30 from the distal end rigid member 20, the side surface portion 31b, having a thin wall thickness, forms a starting point, thus being easily pushed down together with the finger hook portion 37.

In other words, when the finger hook portion 37 is pushed down, a force in a shearing direction is applied to the side surface portion 31b. At this point of operation, the side surface portion 31b deforms to be pushed down and outward due to a thin wall thickness and low rigidity. Therefore, the distal end cover 30 can be easily removed from the distal end rigid member 20.

In such a case, a load is applied to the finger hook portion 37 in the outward direction by the person's finger F, and a force in a tensile direction along a surface of the front surface portion 31a is applied to the front surface portion 31a. The front surface portion 31a has a thin wall thickness and hence, when a load is applied to the finger hook portion 37, the front surface portion 31a easily deforms to be stretched.

Therefore, the front surface portion 31a is pulled toward the finger hook portion 37, thus being deformed, and the locking pawl 34 of the cover body 31 is removed from the engagement groove 23a of the second arm portion 23 of the distal end rigid member 20.

When the distal end cover 30 is further rotated about the longitudinal axis X, the locking pawl 33 of the cover body 31 is removed from the engagement groove 22a of the first arm portion 22 of the distal end rigid member 20. With such operations, the distal end cover 30 is removed from the distal end rigid member 20.

The distal end cover 30 is configured to be prevented from being broken at the time of being deformed when the locking pawl 34 is removed from the engagement groove 23a. The distal end cover 30 may be configured such that when the distal end cover 30 is further deformed, the front surface portion 31a, the side surface portion 31b, or the like is broken to allow the distal end cover 30 to be removed from the distal end rigid member 20.

When no outward load is applied to the finger hook portion 37, the front surface portion 31a suppresses deformation of the side surface portion 31b in a direction in which the side surface portion 31b is pushed down and outward. In other words, the entire surface portion 31a forms a deformation suppressing portion that restricts pushing down of the side surface portion 31b. With such a configuration, it is possible to prevent the distal end cover 30 from unexpectedly falling off from the distal end rigid member 20 when the endoscope 1 is in use.

The finger hook portion 37 is provided to extend to a position that covers the locking pawl 34 formed along the up-and-down direction orthogonal to the longitudinal axis X. In other words, the finger hook portion 37 is formed up to a position where the locking pawl 34 is included in cross section taken in the lateral direction orthogonal to the longitudinal axis X.

With such a configuration, when a load is applied to the finger hook portion 37 in the outward direction by the person's finger F, the locking pawl 34 is also pushed down with deformation of the side surface portion 31b and hence, the distal end cover 30 can be easily removed from the engagement groove 23a of the second arm portion 23.

Figure 18:
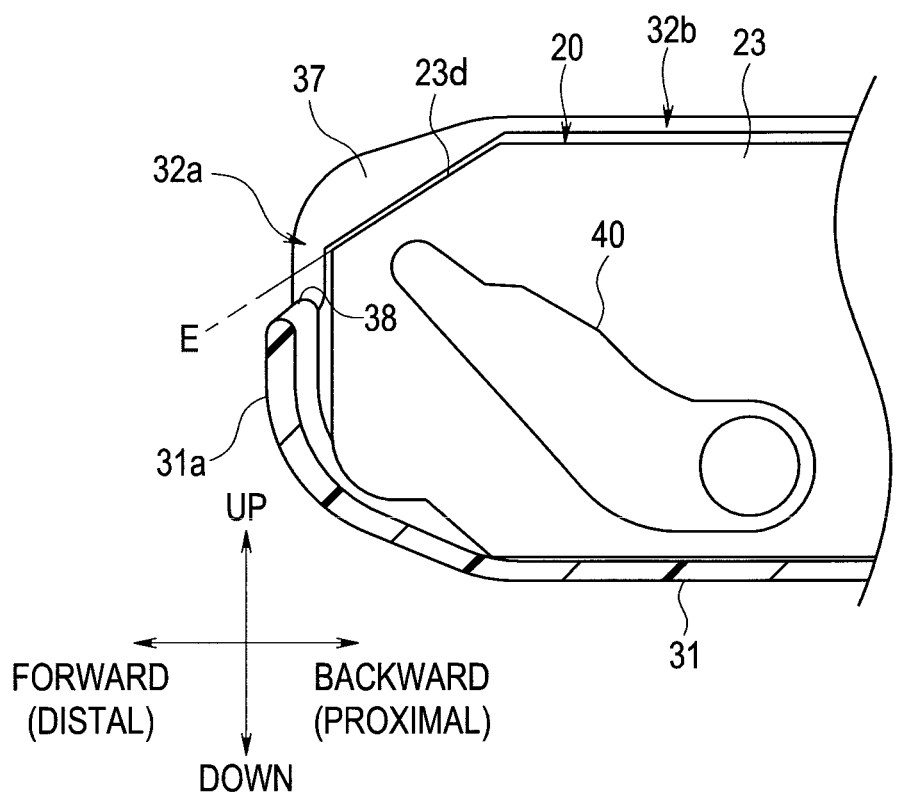
FIG. 18 is a longitudinal cross-sectional view for describing the configuration of the main part of the distal end cover mounted on the distal end rigid member.

As shown in FIG. 18, in the distal end cover 30, the opening 32 includes the distal end opening 32a which extends to the front surface portion 31a. The finger hook portion 37 is a thick wall portion formed to extend to a side portion of the distal end opening 32a. The finger hook portion 37 is formed such that a distal end side in a direction along the longitudinal axis X has a larger wall thickness than a proximal end side.

The distal end opening 32a is formed to extend to a point below an extension line E of a slope 23d in the state where the distal end cover 30 is mounted on the distal end rigid member 20. The slope 23d is a distal end upper surface formed on the distal end side of the second arm portion 23.

Therefore, the distal end cover 30 is configured to allow the person's finger F to enter the distal end cover 30 up to a distal end side of the finger hook portion 37 and hence, the person's finger F can easily come into contact with the finger hook portion 37 to apply a load. In other words, the person's finger F can easily hook on the finger hook portion 37 and hence, the distal end cover 30 can be easily removed from the distal end rigid member 20 by removing the locking pawl 34 of the cover body 31 from the engagement groove 23a.

Figure 19:
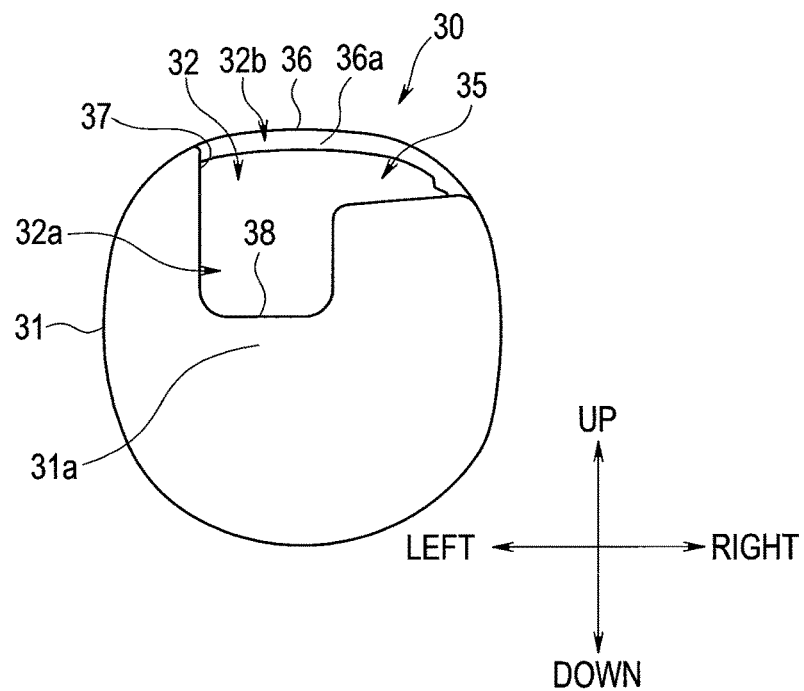
FIG. 19 is a front view for describing the configuration of the main part of the distal end cover.

As shown in FIG. 18 and FIG. 19, the distal end opening 32a of the distal end cover 30 has a substantially rectangular shape. The distal end cover 30 includes an upper end portion 38 extending substantially linearly in the lateral direction of the front surface portion 31a forming one side of the distal end opening 32a. The upper end portion 38 has an arc shape in cross section taken along the longitudinal axis X.

With such a configuration, when the person's finger F access the finger hook portion 37 from the distal end opening 32a, the person's finger F can easily hook on the finger hook portion 37 and hence, an operation of removing the distal end cover 30 is facilitated.

The upper end portion 38 is a substantially flat portion having a substantially linear shape in the lateral direction orthogonal to the longitudinal axis X. By causing the upper end portion 38 of the distal end cover 30 to have a substantially linear shape and to be substantially flat as described above, it is possible to achieve a structure where when an outward load is applied to the finger hook portion 37 to remove the distal end cover 30 from the distal end rigid member 20, the front surface portion 31a forming the deformation suppressing portion, which receives a force in the tensile direction, is prevented from being easily broken.

Further, by causing the upper end portion 38 of the distal end cover 30 to have a substantially linear shape and to be substantially flat, it is possible to achieve a structure where even when the distal end cover 30 is mounted on the distal end rigid member 20, the front surface portion 31a is prevented from being easily broken. The upper end portion 38 may have a streamlined shape instead of a substantially linear shape.

The front surface portion 31a has a substantially uniform wall thickness and has a planar shape. Accordingly, it is possible to achieve a structure where when the distal end cover 30 is mounted on or removed from the distal end rigid member 20, the front surface portion 31a forming the deformation suppressing portion is prevented from being easily broken. In other words, the front surface portion 31a is caused to have a substantially uniform thickness and hence, there is no portion where a wall thickness is locally thin or thick. Accordingly, it is possible to suppress breakage of the front surface portion 31a caused by a force in the tensile direction generated in the front surface portion 31a.

Figure 20:
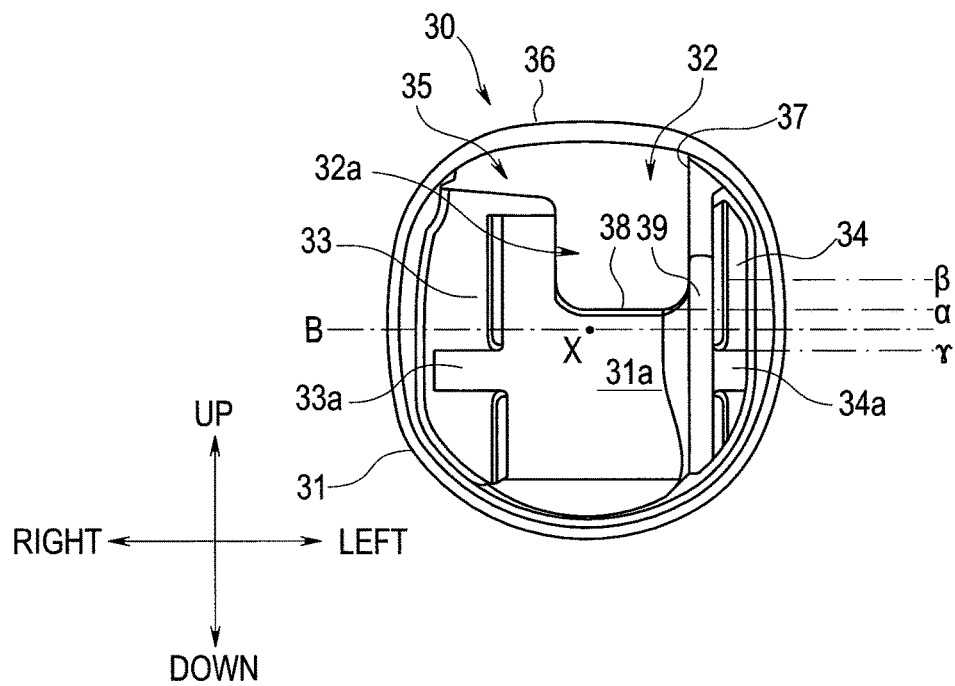
FIG. 20 is a back view for describing the configuration of the main part of the distal end cover.

As shown in FIG. 20, the distal end cover 30 includes an extension portion 39 on the inner surface of the cover body 31. The extension portion 39 extends from the finger hook portion 37 toward the distal end side. In other words, the finger hook portion 37 and the extension portion 39 form one thick wall portion. The extension portion 39 increases rigidity of a portion in the vicinity of the finger hook portion 37, thus preventing the finger hook portion 37 from being pushed down and outward to prevent removal of the locking pawl 34 from the engagement groove 23a. Such a configuration can prevent the distal end cover 30 from falling off from the distal end rigid member 20. It is preferable that the thick wall portion include the extension portion 39. However, only the finger hook portion 37 may be provided without forming the extension portion 39.

The front surface portion 31a and the side surface portion 31b have a smaller wall thickness and lower rigidity than the finger hook portion 37 and the extension portion 39 and hence, when a load for causing the finger hook portion 37 to be pushed down and outward is applied to the finger hook portion 37 by the person's finger F, the front surface portion 31a and the side surface portion 31b deform more easily. Therefore, the locking pawl 34 can be easily removed from the engagement groove 23a.

The upper end portion 38 is located at a position below a center of the locking pawl 34 in a height direction (up-and-down direction) (see extension axes $\alpha$, $\beta$ in the lateral direction in the drawing). With such a configuration, it is possible to increase a height of the distal end opening 32a (a distance in the up-and-down direction).

In other words, when an outward load is applied to the finger hook portion 37 by the person's finger F, the distal end cover 30 is easily pushed down in a direction in which the locking pawl 34 is removed from the engagement groove 23a, thus being easy to remove from the distal end rigid member 20.

A lower end of the locking pawl 34 forming an upper end of the rotation stopping portion 34a (see extension axis y in the lateral direction in the drawing) is located at a position below the upper end portion 38 (extension line $\alpha$) of the front surface portion 31a. In other words, the locking pawl 34 is formed on the inner surface of the cover body 31 such that a portion of the locking pawl 34 is located at a position below the upper end portion 38 of the front surface portion 31a.

With such a configuration, in the distal end cover 30, a portion of the cover body 31 up to the lower end of the locking pawl 34 is prevented from being easily deformed. Therefore, the distal end cover 30 is prevented from easily falling off from the distal end rigid member 20 when the endoscope 1 is in use.

The rotation stopping portions 33a, 34a are located at positions below the upper end portion 38. If the rotation stopping portions 33a, 34a are located at positions above the upper end portion 38, a structure is obtained where the locking pawls 33, 34 have small lengths and the rotation stopping portions 33a, 34a are positioned on an upper side. Therefore, the locking pawls 33, 34 are easily removed from the respective engagement grooves 22a, 23a. In other words, the distal end cover 30 easily falls off from the distal end rigid member 20.

For this reason, in the distal end cover 30, the rotation stopping portions 33a, 34a are located at positions below the upper end portion 38 to form the locking pawls 33, 34 up to positions below the upper end portion 38 by increasing lengths of the locking pawls 33, 34.

With such a configuration, the distal end cover 30 can increase an engagement amount between the locking pawls 33, 34 and the engagement grooves 22a, 23a and hence, it is possible to prevent the distal end cover 30 from falling off from the distal end rigid member 20 when the endoscope 1 is in use.

The rotation stopping portions 33a, 34a are formed at positions close to an axis B along the lateral direction orthogonal to the longitudinal axis X. The distal end cover 30 has a substantially circular outer shape, and a portion of the distal end cover 30 with which the distal end rigid member 20 engages has a substantially rectangular shape. Therefore, by forming the rotation stopping portions 33a, 34a at positions close to a center in the up-and-down direction, it is possible to increase lengths of the rotation stopping portions 33a, 34a in the lateral direction.

Therefore, by increasing the lengths of the rotation stopping portions 33a, 34a in the lateral direction by forming the rotation stopping portions 33a, 34a at positions near the center, it is possible to increase an engagement amount between the rotation stopping portions 33a, 34a and the first and second ribs 22b, 23b. With such a configuration, the distal end cover 30 is prevented from easily rotating relative to the distal end rigid member 20 and hence, it is possible to prevent the distal end cover 30 from falling off from the distal end rigid member 20.

The distal end cover 30 of the endoscope 1 of the present embodiment described above can be removed from the distal end rigid member 20 without breaking the cover body 31 and the cover body 31 is prevented from being easily broken. Accordingly, it is possible to prevent a situation where the distal end cover 30 is brought into an unusable state against intention of a user.

As described above, in the endoscope 1, there is no possibility of the distal end cover 30 being easily broken against the intention of a user and hence, it is possible to prevent a situation where the distal end cover 30 is brought into an unusable state against the intention of the user.

The technique of the endoscope 1 described above is applicable to either a reusable endoscope or a single-use endoscope.

The present disclosure is not limited to the above-mentioned embodiment and modification, and various modifications are conceivable in the implementation stage without departing from the gist of the present disclosure. Further, the above-described embodiment and modification include inventions at various stages, and various inventions may be extracted by an appropriate combination of a plurality of components disclosed.

For example, even if some components are deleted from all components shown in the embodiment and the modification, a configuration from which some components are deleted may be extracted as an embodiment according to the present disclosure provided that the configuration can solve the problem described and can obtain effects described.

What is claimed is:

1. A distal end cover comprising:
a cover body having a bottomed cylindrical shape, the cover body including a first body portion and a second body portion forming a cylindrical peripheral surface;
a first opening formed in the first body portion and the second body portion;
a second opening formed on a side opposite to the first body portion with respect to the second body portion, the second opening being configured to receive a distal end portion of an insertion portion of an endoscope, a longitudinal axis of the distal end cover being parallel or coincident with a longitudinal axis of the insertion portion in a state in which the distal end cover is mounted on the distal end portion of the insertion portion;
a finger hook portion provided in the second body portion and forming a portion of the first opening;
a first thin wall portion provided in the first body portion and forming a portion of the first opening; and
a second thin wall portion provided in the second body portion,
wherein, in a state in which a load is applied to the finger hook portion to expand the first opening, the distal end cover is configured such that a force in a tensile direction is applied to the first thin wall portion and a force in a shearing direction is applied to the second thin wall portion.

2. The distal end cover according to claim 1, wherein the first thin wall portion forms a portion of the first opening, and has a wall thickness smaller than a wall thickness of the finger hook portion.

3. The distal end cover according to claim 2, wherein the second thin wall portion has a wall thickness smaller than the wall thickness of the finger hook portion.

4. The distal end cover according to claim 3, wherein the second thin wall portion and the finger hook portion are provided on a same side of a plane that includes the longitudinal axis of the distal end cover and is orthogonal to the first opening.

5. The distal end cover according to claim 3, wherein the wall thickness of the second thin wall portion is smaller than the wall thickness of the first thin wall portion.

6. The distal end cover according to claim 2, wherein the wall thickness of the first thin wall portion is uniform.

7. The distal end cover according to claim 2, wherein the first thin wall portion forms one side of the first opening, and has an end portion having a streamlined shape or a linear shape.

8. The distal end cover according to claim 1, further comprising a locking portion that protrudes from an inner surface of the second body portion in a direction intersecting with the longitudinal axis of the distal end cover, the locking portion being configured to engage with the distal end portion of the insertion portion to prevent the distal end cover from falling off of the distal end portion.

9. The distal end cover according to claim 8, wherein the first thin wall portion has an end portion forming one side of the first opening,
the distal end cover extends in a height direction that is orthogonal to the longitudinal axis, the height direction extending from a first side at which the first opening is formed to a second side opposite to the first side, and
in a cross section orthogonal to the longitudinal axis, the end portion is located at a position in between the second side and a center of the locking portion in the height direction.

10. The distal end cover according to claim 8, wherein the first thin wall portion has an end portion forming one side of the first opening,
the distal end cover extends in a height direction that is orthogonal to the longitudinal axis, the height direction extending from a first side at which the first opening is formed to a second side opposite to the first side,
the locking portion extends in the height direction from a first locking portion side, closer to the first side of the distal end cover, to a second locking portion side, closer to the second side of the distal end cover, and
in a cross section orthogonal to the longitudinal axis, the end portion is located at a position in between the second locking portion side and the first side of the distal end cover in the height direction.

11. The distal end cover according to claim 8, further comprising:
a rotation restricting portion configured to engage with the distal end portion of the insertion portion to restrict rotation of the distal end cover about the longitudinal axis thereof relative to the distal end portion, the rotation restricting portion being a recessed portion formed on the inner surface of the second body portion and recessed in a direction intersecting with the longitudinal axis,
wherein
the first thin wall portion has an end portion forming one side of the first opening,
the distal end cover extends in a height direction that is orthogonal to the longitudinal axis, the height direction extending from a first side at which the first opening is formed to a second side opposite to the first side, and in a cross section orthogonal to the longitudinal axis, the rotation restricting portion is located at a position in between the end portion and the second side of the distal end cover in the height direction.

12. The distal end cover according to claim 8, wherein
the distal end cover extends in a height direction that is orthogonal to the longitudinal axis, the height direction extending from a first side at which the first opening is formed to a second side opposite to the first side, and
in a cross section orthogonal to the longitudinal axis, a portion of the finger hook portion is formed at a position closer to the first side than the locking portion is to the first side in the height direction.

13. The distal end cover according to claim 1, wherein
the finger hook portion is formed along the longitudinal axis of the distal end cover.

14. The distal end cover according to claim 13, further comprising:
an extension portions formed on an inner surface of the cover body, the extension portion extending from the finger hook portion toward the first body portion.

15. The distal end cover according to claim 1, wherein
the first thin wall portion is configured to be stretched due to the force in the tensile direction, and
the second thin wall portion is configured to be pushed outwards due to the force in the shearing direction.

16. An endoscope comprising:
an insertion portion having a longitudinal axis and configured to be inserted into a subject, the insertion portion including a distal end portion provided at a distal end thereof; and
a distal end cover detachably mounted on the distal end portion, wherein
the distal end cover includes
a cover body having a bottomed cylindrical shape, the cover body including a first body portion and a second body portion forming a cylindrical peripheral surface,
a first opening formed to communicate with the first body portion and the second body portion,
a second opening formed on a side opposite to the first body portion with respect to the second body portion, the distal end portion being inserted into the second opening,
a finger hook portion provided in the second body portion and forming a portion of the first opening,
a first thin wall portion provided in the first body portion and forming a portion of the first opening,
a second thin wall portion provided in the second body portion, and
in a state in which a load is applied to the finger hook portion to expand the first opening, the distal end cover is configured such that a force in a tensile direction is applied to the first thin wall portion and a force in a shearing direction is applied to the second thin wall portion.

17. The endoscope according to claim 16, further comprising:
a raising base provided in the distal end portion, and configured to change a protruding direction of a treatment instrument inserted through the insertion portion; and
a locking portion provided in the distal end cover and protruding from an inner surface of the second body portion in a direction intersecting with the longitudinal axis to engage with the distal end portion, wherein
the raising base is exposed through the first opening,
the first thin wall portion forms a portion of the first opening, and has a wall thickness smaller than a wall thickness of the finger hook portion,
the second thin wall portion has a wall thickness smaller than the wall thickness of the finger hook portion, and
the second thin wall portion and the finger hook portion are provided on a same side of a plane that includes the longitudinal axis and is orthogonal to the first opening.

* * * * *